United States Patent
Vyas et al.

(10) Patent No.: US 7,189,557 B2
(45) Date of Patent: Mar. 13, 2007

(54) PROCESS FOR THE INTRACELLULAR OVER-PRODUCTION OF STREPTOKINASE USING GENETICALLY ENGINEERED STRAIN OF E. COLI

(75) Inventors: Vinay Venkatrao Vyas, Chandigarh (IN); Govindan Rajamohan, Chandigarh (IN); Ramandeep, Chandigarh (IN); Kanak Lata Dikshit, Chandigarh (IN)

(73) Assignee: Council of Scientific & Industrial Research, New Delhi (IN)

( * ) Notice: Subject to any disclaimer, the term of this patent is extended or adjusted under 35 U.S.C. 154(b) by 172 days.

(21) Appl. No.: 10/746,046

(22) Filed: Dec. 29, 2003

(65) Prior Publication Data

US 2005/0142653 A1    Jun. 30, 2005

(51) Int. Cl.
*C12N 1/12* (2006.01)
*C12N 1/20* (2006.01)
*C12N 15/00* (2006.01)
*A61K 39/08* (2006.01)
*A01N 63/00* (2006.01)

(52) U.S. Cl. .................. 435/252.8; 424/93.1; 424/93.2; 424/93.4; 424/241.1; 424/282.1; 435/41; 435/69.1; 435/70.1; 435/71.1; 435/216; 435/243; 435/252.1; 435/252.3; 435/252.33; 435/320.1

(58) Field of Classification Search ............... 424/93.1, 424/93.2, 93.4, 241.1, 282.1; 435/41, 69.1, 435/70.1, 71.1, 216, 243, 252.1, 252.3, 252.33, 435/320.1, 252.8
See application file for complete search history.

(56) References Cited

U.S. PATENT DOCUMENTS 5,187,098 A * 2/1993 Malke et al. ............ 435/320.1

OTHER PUBLICATIONS

Dao et al. 1985. Appl. Environ. Microbio. vol. 49(1): 115-119.*

* cited by examiner

*Primary Examiner*—Bruce R. Campell
*Assistant Examiner*—J. Hines
(74) *Attorney, Agent, or Firm*—Nixon Peabody LLP; Donald R. Studebaker

(57) ABSTRACT

An improved process for the production of streptokinase using a genetically engineered strain of *Escherichia coli* which overproduces streptokinase intracellularly and more particularly, the overall process disclosed herein, concerns with an improvement in the fermentative production of streptokinase using an optimized growth medium mainly comprised of simple salts and trace-elements; thus, in principal, the present process constitutes an improved and more economical means for the production of streptokinase which may be useful in thrombolytic therapy.

2 Claims, No Drawings

PROCESS FOR THE INTRACELLULAR OVER-PRODUCTION OF STREPTOKINASE USING GENETICALLY ENGINEERED STRAIN OF E. COLI

FIELD OF THE INVENTION

The present invention disclosed herein, relates to an improved process for the production of streptokinase using a genetically engineered strain of E. coli PSK4 deposited at the Microbial Type Culture Collection, at the Institute of Microbial Technology, Chandigarh, India, bearing Accession number MTCC 5120, which overproduces streptokinase intracellularly. More particularly, the overall process disclosed herein, concerns with an improvement in the fermentative production of streptokinase using an optimized growth medium mainly comprised of simple salts and trace-elements. Thus, in principal, the present process constitutes an improved and more economical means for the production of streptokinase which may be useful in thrombolytic therapy.

BACKGROUND AND PRIOR ART OF THE INVENTION

Streptokinase, an efficient activator of fibrinolysis, is routinely utilized in clinical medicine for thrombolytic therapy for the treatment of diverse circulatory disorders, e.g., pulmonary thrombo-embolism, deep vein thrombosis, and myocardial infarction. It exerts its fibrinolytic effects through activation of an inert blood Zymogen, Plasminogen (PG), an active serine protease, Plasmin (PN), which attacks on fibrin to degrade it into soluble degradation products. It has been clearly demonstrated, particularly in the case of myocardial infarction, that in the actual management of the disease, streptokinase is as efficacious as its more expensive clot-dissolving alternatives, such as Urokinase (UK) and tissue-Plasminogen activator (tPA). Its utility in thrombolytic therapy is well established. Reference maybe made to the publications of Paques, E. P., 1986, Haemostasis, Vol. 16, Suppl. 3, 21; ISIS-3 (Third International Study of Infarct Survival: A randomized comparison of streptokinase vs. tissue plasminogen activator vs. anistreplase and of asprin plus heparin alone among 41,299 cases of suspected acute myocardial infarction) Collaborative Group, 1992, Lancet 339,753.

Streptokinase is a single chain 47-kD protein, consisting of 414 amino acid resides (reference may be made in the context of the biochemical properties of Streptokinase to the review article by Castellino, F. J., 1981, Chem Rev. 81, 431). It is naturally produced and secreted by various strains of hemolytic *streptococci* along with several other unwanted toxic products, e.g. deoxyribonucleases, streptolysin or hyaluronidase and proteases, which makes the process of purifying the desired protein difficult. On the other hand it has not yet been possible to obtain genetically improved strains from these hosts due to the lack of a developed methodology for the gene transfer. Considering its therapeutic applicability and clinical implications in thrombolytic therapy, attempts have been made in the past to search for an alternative source of Streptokinase production through recombinant routes. Reference is made to the publication of Malke and Ferretti, Proceedings of the National Academy of Sciences, USA, Vol. 81, p351, 1984; Hagenson et al., 1989, Enzyme and Microbial Technology, Vol 11, 650; Estrada et al., 1992, Biotechnology Vol 10, 1138; Reference may also be made to U.S. Pat. Nos. 5,296,366, 5,240,845, 4,764,469, 2,043,953, Japanese Patent Number 2020828, European Patent No. 489201, and Cuban Patent No. 90. In the work reported in aforesaid publications and patents, the gene encoding for SK has been isolated from its natural host, *Streptococcus* and cloned into various heterologous hosts, e.g., *E. Coli, Bacillus* and yeasts.

In order to improve the yield of Streptokinase, in particular, the gene which determines streptokinase C, A and G (References may be made to the publications of Huang et al 1989, Molecular Microbiology Vol 2(3), 197; and Estrada et al, 1992, Biotechnology Vol 10, 1138;) were cloned and expressed in *E. coli* as well as *Streptococcus sanguis* (Reference may be made to the publication of Malke et al., 1984, Molecular and General Genetics Vol 1%, 360). In both the cases, protein levels of 0.64 mg/l and 40 µg/l, respectively, were obtained. In the case of *E. coli*, 94% of the protein recovered was in the periplasmic space and 6% in the cytosol, whereas, in *S. sanguis* all the enzyme was found extracellularly. Moreover, many clones producing streptokinase were very unstable owing to some lethal activity of the gene product or protein secretion. More recently, intracellular production of streptokinase has been reported in *E. Coli* (Reference may be made to the publication of Xue-Wu Zhang et al, 1999, Enzyme and Microbial Technology, Vol 24,647) where 300–400 mg/ml SK protein has been obtained from one liter cell culture of *E. coli* using a rich and complex cell growth medium.

More often recombinant *E. coli* strain, developed for the overproduction of streptokinase, exhibited low cell density and biomass which affected the overall yield of the protein product. Production of recombinant streptokinase in the methylotrophic yeast, *Pichia pastoris*, has been attempted by Philips Petroleum Company (Reference may be made to the publication of Hagenson et al., 1989, Enzyme and Microbial Technology, Vol 11, 650) and Cuban group (Reference may be made to the publication of Estrada et al., 1992, Biotechnology Vol 10, 1138; and Cuban Patent Number 90), where 1.8 mg/l and 1.0 g/l, respectively, of SK has been obtained using continuous fermentation and rich growth medium comprising of complex and expensive ingredients. Using a genetically engineered strain of *E. coli* 645 mg/l of SK production (Reference may be made to the publication of Xue-Wu Zhang et al, 1999, Enzyme and Microbial Technology, Vol. 24, 647) has been reported under fermentative condition using a rich growth medium.

OBJECT OF THE INVENTION

Thus the prime objective of the present invention is to develop an improved and economical process for the production of streptokinase using a genetically engineered strain of *E. coli* which produces this protein intracellularly.

Yet another objective of the invention is to prepare a piece of Deoxyribonucleic Acid (DNA) carrying complete genetic information for the production of streptokinase inside the cell of recombinant *E. coli* obtained as above and to prepare an expression plasmid DNA (pSK4) carrying the genetic information for the production of Streptokinase in a suitable *E. coli* host. In this plasmid pSK4, p denotes plasmid and SK denotes streptokinase. It has been deposited in the Microbial Type Culture Collection at the Institute of Microbial Technology, under the Accession number MTCC 5120 on Nov. 25, 2003.

Yet another objective of this is to design a process for obtaining large quantity of cell biomass of genetically engineered *E. coli* PSK4 (Accession No. MTCC 5120) using fermentative processes in order to improve the overall production of streptokinase and to recover large amounts of streptokinase during subsequent downstream processing.

SUMMARY OF THE INVENTION

The present process pertains to the development of an improved and economical process for the production of streptokinase using a genetically engineered strain of *E. coli* PSK4 bearing International Accession number MTCC 5120 carrying a replicative plasmid vector, capable of producing streptokinase intracellularly in high yields. Streptokinase so obtained exhibits biological properties, e.g., clot dissolution and plasminogen activation characteristics, similar to natural streptokinase. Further a fermentation process for the high-cell density cell culture of this recombinant *E. coli* strain has been developed utilizing an inexpensive growth medium composition, which results in a higher cell biomass yielding higher recovery of streptokinase from the cell extract. Following these steps, high-level of streptokinase can be obtained from the cell culture of *E. coli* (Accession No. MTCC 5120) which is biologically active and may be useful for therapeutic purposes.

DETAILED DESCRIPTION OF THE INVENTION

The present invention provides an improved process for the production of intracellular streptokinase using a genetically engineered strain of *E. coli* (deposited at the Microbial Type Culture Collection at the Institute of Microbial Technology, Sector 39-A, Chandigarh—160 036, India under Accession No. MTCC 5120) overproducing streptokinase intracellularly following an optimized batch and fed-batch fermentation regime using simple and inexpensive medium components. The process comprises of:

1. Preparation of a piece of DNA carrying genetic information for the production of streptokinase through, recombinant processes or through a synthetic approach following known procedures.
2. Integration of the above piece of DNA on a suitable replicable plasmid vector through known recombinant processes to prepare a replicable expression plasmid vector, capable of producing streptokinase in a suitable host under appropriate conditions.
3. Introduction of plasmid DNA prepared at step 2, into an appropriate host cell such as such as *E. coli, B. subtilis*, or Yeast
4. Adaptation of the host cell prepared at step 3 into a growth medium of defined composition consisting of basal salts, trace elements and carbon source.
5. Adjustment of aeration in the range 0% to 100% dissolved oxygen, agitation in the range 50 to 1000 revolutions per minute and pH in the range 5 to 8.
6. Addition of antibiotic such as Kanamycin, Ampicillin and the like, in the range 1 to 1000 microgram per milliliter in the fermenter
7. Addition of seed culture of the host cell in the range 0.1% to 10% carrying the desired expression plasmid into the fermentation medium
8. Cultivating in the fermenter for a period ranging from 6 to 24 hours.
9. Optionally feeding additional nutrients to the fermentation medium at time intervals ranging from 15 minutes to 90 minutes and at rates ranging from 100 mL per hour to 1000 mL per hour to enhance biomass yields
10. Addition of the inducer (IPTG) in the range 0.01 mM to 10 mM, after sufficient cell biomass is attained.
11. Harvesting of cell culture broth by conventional centrifugation and/or microfiltration.
12. Lysis/breakage of *E. coli* cells through chemical lysis, sonication, bead mill or through French Pressure cell
13. Isolation and resolubilization of streptokinase inclusion bodies from fermentation broth
14. Isolation and separation of streptokinase protein following conventional chromatographic steps.

In yet another embodiment of the present invention, wherein the overall process developed and disclosed herein is primarily based on the use of a genetically engineered strain of *E. coli* carrying a plasmid DNA encoding for the production of streptokinase for the high level fermentative production of streptokinase level using defined growth medium and physiological parameters such as aeration, pH, induction conditions, nutrient feed etc. Large scale production of streptokinase using recombinant strains of *E. coli* (Accession No. MTCC 5120) has been done mainly using complex growth medium for the recovery of large quantities of streptokinase. Using a specifically designed expression plasmid, intracellular production of SK has been obtained under fermentation condition which yielded about 200–330 mg SK/L cell culture.

In still another embodiment of the present invention, wherein a piece of DNA carrying genetic information for the production of streptokinase has been retrieved from the recombinant plasmid construct, pJKD-21, carrying an open-reading frame cassette for the production of streptokinase.

In still another embodiment of the present invention, wherein the expression plasmid was constructed by preparation of a piece of DNA obtained as above, and carrying the genetic information for the production of streptokinase through known recombinant or synthetic processes and integrated on to a suitable replicable plasmid like pET-9A again through known recombinant techniques to prepare a replicable expression plasmid vector.

In still another embodiment of the present invention, wherein the said plasmid expression vector was then introduced into an appropriate host like *E. coli* or *B. subtilis* or yeast using known transformation techniques and adapted on to a synthetic medium comprising of a sole carbon source, basal salts and trace elements whose composition is as follows: glycerol as carbon source in the range 10–35 g/L, Potassium phosphate in the range 5–20 g/L, Ammonium phosphate in the range 2–6 g/L. Magnesium sulphate in the range 1–3 g/L, Citric acid in the range 1–2 g/L, EDTA in the range 5–10 mg/L, Cobalt chloride in the range 2–4 mg/L, Manganese chloride in the range 10–20 mg/L, Copper chloride in the range 0.5–2.5 mg/L, Boric acid in the range 2–5 mg/L, Sodium molybdate in the range 1–5 mg/L, Zinc acetate in the range 5–25 mg/L, Ferric chloride in the range 50–100 mg/L, and Thiamine hydrochloride in the range 4–8 mg/L.

In still another embodiment of the present invention, wherein this adapted culture was then cultured in the fermenter at a pH range of 5–8, aeration range of 0% to 100% dissolved oxygen, and agitation range of 50 to 1000 revolutions per minute on the above synthetic medium.

In still another embodiment of the present invention, wherein 0.1% to 10% of the seed inoculum also prepared using this synthetic medium was inoculated into the fermenter containing sterile synthetic medium.

In still another embodiment of the present invention, wherein antibiotic such as kanamycin, ampicillin and the like was added in the range 1 to 1000 microgram per milliliter to the seed medium and fermetation medium prior to the addition of culture organism. After 6 to 24 hours of growth, inducer isopropyl-β D thiogalactopyranoside (IPTG) in the range 0.01 mM to 10 mM was added to induce the culture to produce streptokinase.

In still another embodiment of the present invention, wherein fermentation was further carried out for a period ranging from 4 to 10 hours and biomass harvested by-conventional centrifugation or micro-filtration.

In still another embodiment of the present invention, wherein the biomass thus obtained was lysed using known techniques of cell lyses and streptokinase inclusion bodies harvested.

In still another embodiment of the present invention, wherein the harvested inclusion bodies of streptokinase were resolubilized in Urea or Guanidine hydrochloride buffers and refolded and purified to obtain enzymatically active and pure streptokinase. In a preferred embodiment, 1.3 kb amplified DNA was joined on suitable expression Plasmid vectors, such as pKK-233-2, pET-9A, Trc-99 etc (ranging from 30–50 copy/cell), preferably pET-9A, which was digested with restriction enzymes such as Nde I, BamHI and the like. In another preferred embodiment, E. coli strains, BL 21DE3, or JM 105, preferably BL 21DE3, have been utilized for carrying plasmid vectors linked with Streptokinase encoding DNA.

In yet another preferred embodiment the trace elements and carbon source were sterilized separately and added to the sterile fermenter containing the basal salt solution. In yet another preferred embodiment additional nutrient feed was added to the fermenter to enhance biomass. A further description of the invention is given in examples below, which should not however be construed to limit the scope of the present invention.

EXAMPLE 1

Preparation of a Replicative Plasmid (pSK4) Expressing of Signal-Peptide Free Streptokinase for the Intracellular Production of Streptokinase in E. Coli (Accession No. MTCC 5120)

The source of DNA for retrieving mature Streptokinase encoding gene, lacking its native signal peptide sequences, was plasmid pJKD-21. 3 µg of plasmid pJKD-21 was digested with 5–10 units each of NdeI and BamHI restriction enzymes using known techniques and incubated at 37° C. for 8 hrs. Reaction was stopped by heating the reaction mixture at 80° C. for 10 minutes and this digested sample was electrophoresed on 1% agarose gel for 1 h at 150 mV. 1.3 kb DNA fragment liberated from the plasmid pJKD-21 was excised from the gel and purified using gene-clean kit. In a parallel reaction, 1 µg of plasmid pET9a (commercially obtained from New England Biolabs) was also digested with 5 and 10 units of NdeI and BamHI, respectively and Incubated at 37° C. for 8–10 hrs. This digest was mixed with 0.5 µg of 1.3 kb DNA fragment of plasmid pJKD-21 in a total volume of 50 µl. This DNA mixture was precipitated at −20° C. in the presence of 100 µl of absolute ethanol and 5 µl of sodium acetate. DNA precipitate was dissolved in 17 µl of water and 3–4 units of T4DNA ligase was added along with its complementary buffer (obtained commercially from New England Biolabs, USA). This reaction mix was incubated at 16° C. for overnight and transformed in E. coli BL21DE3 through known transformation procedure. Transformed cells were plated on LB (Luria-Broth) plates carrying 20 µg/ml Kanamycin antibiotic and incubated at 37° C. for overnight. 10 individual colonies were picked out in 10 ml LB medium carrying 20 µg of kanamycin and incubated at 37° C. for 4–5 h till the cell OD reached to 0.5, after that 0.01 mM IPTG was added and cells were further incubated for overnight. The cells were pelleted by centrifugation and analyzed on 10% SDS-PAGE. The colonies exhibited an intense 47 kD protein band which was not present in the control cells which were transformed with the control plasmid pET9a. The selected clone was designated as pSK4 and deposited in the Microbial Type Culture Collection, Institute of Microbial Technology, Chandigarh, under the Accession number MTCC 5120. This was subjected to fermentation to realize the production level of Streptokinase and its biological characterization.

EXAMPLE 2

Adaptation of the Recombinant E. Coli to a Synthetic Medium

E. coli (Accession No. MTCC 5120 growing on complex media like Luria Broth (LB) was adapted to synthetic medium comprising of glycerol as carbon source 25 g/L, Potassium phosphate 13 g/L, Ammonium phosphate 4 g/L, Magnesium sulphate 1.2 g/L, Citric acid 1.7 g/L, EDTA 8.4 mg/L, and trace element solution (1 mL–10 mL) containing: trace quantities of Cobalt chloride, Manganese chloride, Copper chloride, Boric acid, Sodium molybdate, Zinc acetate, Ferric chloride, and Thiamine hydrochloride. 100 µl of LB grown culture in the early stationary phase of growth was inoculated into a 100 mL shake flask containing 10 mL of pre-warmed synthetic medium containing 50 µg/mL Kanamycin and incubated at 37° C. at 100 RPM in a rotary shaker for 8 hours. 100 µL of this culture was inoculated into another 100 mL shake flask containing 10 mL of pre-warmed synthetic medium containing 50 µg/µl Kanamycin and incubated at 37° C. at 100 RPM in a rotary shaker for 8 hours. 1 ml of this culture was further inoculated into a 500 mL shake flask containing 50 mL of pre-warmed synthetic medium containing 50 µg/µl Kanamycin and incubated for 8 hours. 500 µl aliquots of this adapted culture was mixed with equal volume of 50% glycerol in 1 ml vials and stored at −70° C. as Glycerol Stocks.

EXAMPLE 3

Preparation of Seed Culture of Recombinant E. Coli for Fermentation

For each fermentation one vial of Glycerol Stock as prepared in Example 2 was inoculated into a 500 mL shake flask containing 50 mL of pre-warmed synthetic medium synthetic medium comprising of glycerol as carbon source 25 g/L, Potassium phosphate 13 g/L, Ammonium phosphate 4 g/L, Magnesium sulphate 1.2 g/L, Citric acid 1.7 g/L, EDTA 8.4 mg/L, and trace element solution (1 mL–10 mL) containing trace quantities of: Cobalt chloride, Manganese chloride, Copper chloride, Boric acid, Sodium molybdate, Zinc acetate, Ferric chloride, and Thiamine hydrochloride. Kanamycin 50 µg/µl was added and incubated for 10 hours and was used as the seed inoculum for all fermentations.

EXAMPLE 4

Batch Fermentation for the Production of Recombinant Streptokinase 2.0 L of basal salt medium comprising of Potassium phosphate 13 g/L, Ammonium phosphate 4 g/L, Magnesium sulphate 1.2 g/L, Citric acid 1.7 g/L, EDTA 8.4 mg/L, were sterilized in a 3 L Chemap fermenter. Glycerol (10–35 g/L) preferably 30 g/L, and trace element solution (1 mL–10 mL) containing trace quantities of: Cobalt chloride, Manganese chloride, Copper chloride, Boric acid. Sodium molybdate, Zinc acetate, Ferric chloride, and Thiamine hydrochloride were all sterilized separately and added to the cooled fermenter and the final volume made up to 2.45 L with sterile distilled water. pH was adjusted to 7.4 using 5N Sodium hydroxide. 50 ug/uL of filter sterilized Kanamycin was added prior to the addition of seed inoculum.

50 mL of seed inoculum as prepared in Example 3 was added to make the volume finally to 2.5 L. The main cultivation was carried out at 37° C. for a period of 12 hrs. pH in the fermenter was maintained at 7.4 by using aqueous ammonia and HCl. Fermenter RPM of 700 and an initial aeration rate of 2.5 L/min was set. RPM was slowly increased to 900 to maintain a minimum dissolved oxygen concentration of 10% air saturation. The fermentation was carried out for 10 hours after which the fermenter was induced with 0.2 mM IPTG when a biomass concentration of 7 g DCW (dry cell weight)/L was achieved in the fermenter. Fermentation was continued for another 4 hours and biomass harvested for streptokinase recovery.

EXAMPLE 5

Fed Batch Fermentation for the Production of Recombinant Streptokinase 2.0 L of basal salt medium comprising of Potassium phosphate 13 g/L, Ammonium phosphate 4 g/L, Magnesium sulphate 1.2 g/L, Citric acid 1.7 g/L, EDTA 8.4 mg/L, were sterilized in a 3 L Chemap fermenter. Glycerol (10–35 g/L) preferably 30 g/L, and trace element solution (1 mL–10 mL) containing trace quantities of: Cobalt chloride, Manganese chloride, Copper chloride. Boric acid, Sodium molybdate, Zinc acetate, Ferric chloride, and Thiamine hydrochloride were all sterilized separately and added to the cooled fermenter and the final volume made up to 2.45 L with sterile distilled water. pH was adjusted to 7.4 using Sodium hydroxide. 50 μg/μl of filter sterilized Kanamycin was added prior to the addition of seed inoculum 50 mL of seed inoculum as prepared in Example 3 was added to make the volume finally to 2.4 L. The main cultivation was carried out at 37° C. pH in the fermenter was maintained at 7.4 by using aqueous ammonia and HCl. Fermenter RPM of 700 and an initial aeration rate of 2.5 L/min was set. RPM was slowly increased to 900 to maintain a minimum dissolved oxygen concentration of 10% air saturation. The fermentation was carried out for 10 hours after which 50 ml of fresh feed consisting of Glycerol 795 g/L, Magnesium sulphate 20 g/L, EDTA 13 mg/L, Cobalt chloride 4 mg/L, Manganese chloride 23.5 mg/L, Copper chloride 2.5 mg/L, Boric acid 5 mg/L, Sodium molybdate 4 mg/L, Zinc acetate 16 mg/L, and Ferric chloride 40 mg/L was added. The fermentation was further carried out for 40 minutes and another 50 ml of fresh feed containing Glycerol 795 g/L, Magnesium sulphate 20 g/L, EDTA 13 mg/L, Cobalt chloride 4 mg/L, Manganese chloride 23.5 mg/L, Copper chloride 2.5 mg/L, Boric acid 5 mg/L, Sodium molybdate 4 mg/L, Zinc acetate 16 mg/L, and Ferric chloride 40 mg/L was added. The fermenter was induced with 1 mM IPTG when a biomass concentration of 18 g DCW (dry cell weight)/L was achieved in the fermenter. Fermentation was continued for another 4 hours and biomass harvested for streptokinase.

EXAMPLE 6

Isolation and Resolubilization of Inclusion Bodies from Fermentation Broth

Fermentation broth was centrifuged at 5000 g for 15 minutes at 4 C, to recover biomass. The cells were washed in a buffer containing (i) 10 mM Tris HCl, pH 8, (ii) 10 mM EDTA, and (iii) 100 mM Sodium chloride and re-centrifuged. The cell pellet was re-suspended in the buffer containing (i) 10 mM Tris HCl, pH 8, (ii) 10 mM EDTA, (iii) 100 mM Sodium chloride, (iv) 1 mM Phenyl methyl sulfonyl fluride. Lysozyme preferably 0.64% was added to the above solution and stirred for 3 hours at 4° C. prior to sonication for 30 minutes. The sonicated solution was centrifuged at 5000 g to obtain streptokinase inclusion bodies.

8 M Urea or 6 M Guanidine HCl was added to the above isolated inclusion bodies and stirred for 24 hours and centrifuged at 5000 g. The supernatant was diluted 100 fold using a buffer containing 0.05 mM Tris at a pH of 7.5 and dialyzed to obtain active recombinant streptokinase.

We claim:
1. A genetically engineered strain of *Escherichia coli* PSK4 deposited in the Microbial Type Culture Collection at the Institute of Microbial Technology, Chandigarh, India, bearing Accession number MTCC 5120.
2. The genetically engineered strain as claimed in claim 1, wherein said strain;
   a) carries a recombinant 4.3 kilobase plasmid pSK4 encoding, 47KDa protein,
   b) the recombinant plasmid having a streptokinase encoding gene fragment, and
   c) carries kanamycin resistant marker which provide Kanamycin resistance.

* * * * *